(12) United States Patent
Huang

(10) Patent No.: US 9,750,610 B2
(45) Date of Patent: Sep. 5, 2017

(54) METHOD AND DEVICE FOR PREPARING ARTIFICIAL BONES OF CEREBRAL CRANIUM FROM POLYETHER ETHER KETONE

(71) Applicant: WUHAN CONSTANT SCIENCE AND TECHNOLOGY LTD., Wuhan (CN)

(72) Inventor: Dengfeng Huang, Wuhan (CN)

(73) Assignee: WUHAN CONSTANT SCIENCE AND TECHNOLOGY LTD., Wuhan (CN)

( * ) Notice: Subject to any disclaimer, the term of this patent is extended or adjusted under 35 U.S.C. 154(b) by 434 days.

(21) Appl. No.: 14/289,671

(22) Filed: May 29, 2014

(65) Prior Publication Data

US 2014/0265015 A1    Sep. 18, 2014

Related U.S. Application Data

(63) Continuation-in-part of application No. PCT/CN2012/071370, filed on Feb. 20, 2012.

(30) Foreign Application Priority Data

Nov. 29, 2011    (CN) .......................... 2011 1 0386538

(51) Int. Cl.
*A61F 2/28*    (2006.01)
*B29C 43/00*    (2006.01)
*A61F 2/30*    (2006.01)

(52) U.S. Cl.
CPC ........ *A61F 2/2875* (2013.01); *A61F 2/30942* (2013.01); *A61F 2002/30948* (2013.01); *A61F 2002/30957* (2013.01)

(58) Field of Classification Search
CPC ......... A61F 2/2875; A61F 2002/30948; B29C 43/003; B29C 2043/522
See application file for complete search history.

(56) References Cited

U.S. PATENT DOCUMENTS 5,274,565 A * 12/1993 Reuben ............... A61F 2/30942
700/182
2004/0156753 A1* 8/2004 Roitman .............. B01J 19/0093
422/504

(Continued)

FOREIGN PATENT DOCUMENTS

CN    2061891 U  *  9/1990
CN    1523530 A  *  8/2004

(Continued)

*Primary Examiner* — Erin Snelting
(74) *Attorney, Agent, or Firm* — Matthias Scholl, PC; Matthias Scholl

(57) ABSTRACT

A method for preparing bones of cerebral cranium, including: a) selecting polyetheretherketone (PEEK) as a raw material according to data obtained by computed tomography (CT) of a patient; b) heating the PEEK material in a heating device to reach a softening point of 260°±10°; c) hot pressing the heated PEEK material obtained in step b) in a forming die, cooling and shaping the PEEK material to yield a blank; d) curing the blank, and placing the blank in a thermostat for removal of internal stress and resilience; e) removing surface crystals and impurities of the blank resulting from the hot pressing; f) mechanically processing the blank according to the CT data of the patient to yield a product having desired size and shape; and g) washing, disinfecting, and packaging the product.

1 Claim, 4 Drawing Sheets

(56) References Cited

U.S. PATENT DOCUMENTS

| | | | |
|---|---|---|---|
| 2007/0185488 A1* | 8/2007 | Pohjonen | A61L 31/06 623/17.16 |
| 2010/0292963 A1* | 11/2010 | Schroeder | A61F 2/30 703/1 |
| 2011/0009879 A1* | 1/2011 | Derrick | A61B 17/3403 606/130 |
| 2012/0203289 A1* | 8/2012 | Beerens | A61B 17/17 606/323 |
| 2013/0004585 A1* | 1/2013 | Crudden | A61L 27/18 424/618 |

FOREIGN PATENT DOCUMENTS

| | | | |
|---|---|---|---|
| CN | 1593670 A | * | 3/2005 |
| CN | 101092059 A | * | 12/2007 |

* cited by examiner

METHOD AND DEVICE FOR PREPARING ARTIFICIAL BONES OF CEREBRAL CRANIUM FROM POLYETHER ETHER KETONE

CROSS-REFERENCE TO RELATED APPLICATIONS

This application is a continuation-in-part of International Patent Application No. PCT/CN2012/071370 with an international filing date of Feb. 20, 2012, designating the United States, now pending, and further claims priority benefits to Chinese Patent Application No. 201110386538.7 filed Nov. 29, 2011. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079.

BACKGROUND OF THE INVENTION

Field of the Invention

The invention relates to a method and device for preparing bones of cerebral cranium using PEEK (polyether ether ketone).

Description of the Related Art

Typically, skull defects are repaired using a titanium mesh plate which has high strength, excellent biocompatibility and is non-toxic. However, titanium does corrode after implantation.

A composite consisting of polymethyl methacrylate (PMMA), a biological carbon fiber or glass fiber, and hydroxyapatite powder or β-tricalcium phosphate powder has been used for the preparation of artificial bones of cerebral cranium by multi-layer cladding and heat pressing. However, these materials are also thought to pose dangers after implantation.

PEEK resin features excellent mechanical performance, good self-lubrication, chemical corrosion resistance, stable insulation performance, flame retardancy, peel resistance, irradiation resistance, X rays permeability, hydrolysis resistance, and easy processing. The mechanical performance of PEEK resin is similar to that of aluminum alloy.

Typically, PEEK for use as human implantation material is processed using mechanical cold method which results in over 70% waste. Thus, conventionally-processed PEEK implantation material is highly priced.

SUMMARY OF THE INVENTION

In view of the above-described problems, it is one objective of the invention to provide a method for preparing bones of cerebral cranium.

It is another objective of the invention to provide a device for preparing bones of cerebral cranium.

In another aspect, the invention provides a use of PEEK for preparation of bones of cerebral cranium.

To achieve the above objective, in accordance with one embodiment of the invention, there is provided a method for preparing bones of cerebral cranium. The method comprises the following steps:

a) selecting polyetheretherketone (PEEK) as a raw material according to computed tomography (CT) data of a patient;

b) heating the PEEK material in a heating device to reach a softening point of 260°±10°;

c) hot pressing the heated PEEK material obtained in step b) in a forming die, cooling and shaping the PEEK material to yield a blank;

d) curing the blank, and placing the blank in a thermostat for removal of internal stress and resilience;

e) removing surface crystals and impurities of the blank resulting from the hot pressing;

f) mechanically processing the blank according to the CT data of the patient to yield a product having desired size and shape; and g) washing, disinfecting, and packaging the product.

In a class of this embodiment, the heating device discriminatively heats different areas of the PEEK material to meet the requirements of temperature and strain force for material deformation according to the CT data of the patient, areas requiring a relatively large deformation are heated at a relatively high temperature, and areas requiring a relatively small deformation is heated at a relatively low temperature.

In a class of this embodiment, the forming die comprises an upper mold comprising an upper needle module and a lower mold comprising a lower needle module. The lower needle module is controlled by a programmable logic controller (PLC) for space regulating and locating according to the CT data. The upper needle module is also regulated correspondingly. The heated PEEK material is placed on the upper mold and processed by the upper and lower needle modules to yield the blank.

In accordance with another embodiment of the invention, there is provided a device for preparing bones of cerebral cranium, comprising: a forming die and a heating device. The forming die comprises an upper mold base, an upper mold, a locating device, a lower mold, a lower mold base, a base frame. The upper mold is fixed on the upper mold base. The lower mold base is fixed on the base frame via a pin bolt. The upper mold is fixed on the lower mold base, and a lower end of the locating device is fixed on the base frame. The upper mold base is fixed on the locating device, and a rear end of the upper mold base is located in a sliding groove of the locating device. The upper mold and the lower mold each comprises a plurality of needle modules. The needle modules are controlled by a first PLC via a displacement sensor. The locating device is perpendicular to the base frame.

In a class of this embodiment, the heating device comprises an upper cover plate, an upper heater, a support bracket, a lower heater, and a base. The support bracket is disposed between the upper heater and the lower heater. The upper heater is disposed under a central area of the upper cover plate. The lower heater is disposed over a central area of the base. The upper heater and the lower heater each comprises a plurality of independent little resistance wires, and a second PLC is connected to the little resistance wires via a temperature sensor.

The invention further provides a method for preparing bones of cerebral cranium comprising employing PEEK as a raw material.

Advantages according to embodiments of the invention are summarized as follows. The method combines the thermal forming and cold processing thereby significantly reducing the PEEK material wastage and saving the medical expenses. The resulting products are made according to the CT data of patients and thus can be tightly integrated with human skull, showing good biocompatibility, and no rejection and side effect are observed.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing a method and device preparing bones of cerebral cranium are described below. It should be noted that the following examples are intended to describe and not to limit the invention.

The invention provides a method for preparing bones of cerebral cranium. The method comprises:
a) selecting polyetheretherketone (PEEK) as a raw material according to computed tomography (CT) data of a patient;
b) heating the PEEK material in a heating device to reach a softening point of 260°±10°;
c) hot pressing the heated PEEK material obtained in step b) in a forming die, cooling and shaping the PEEK material to yield a blank;
d) curing the blank, and placing the blank in a thermostat for removal of internal stress and resilience;
e) removing surface crystals and impurities of the blank resulting from the hot pressing;
f) mechanically processing the blank according to the CT data of the patient to yield a product having desired size and shape; and
g) washing, disinfecting, and packaging the product.

Figure 4:
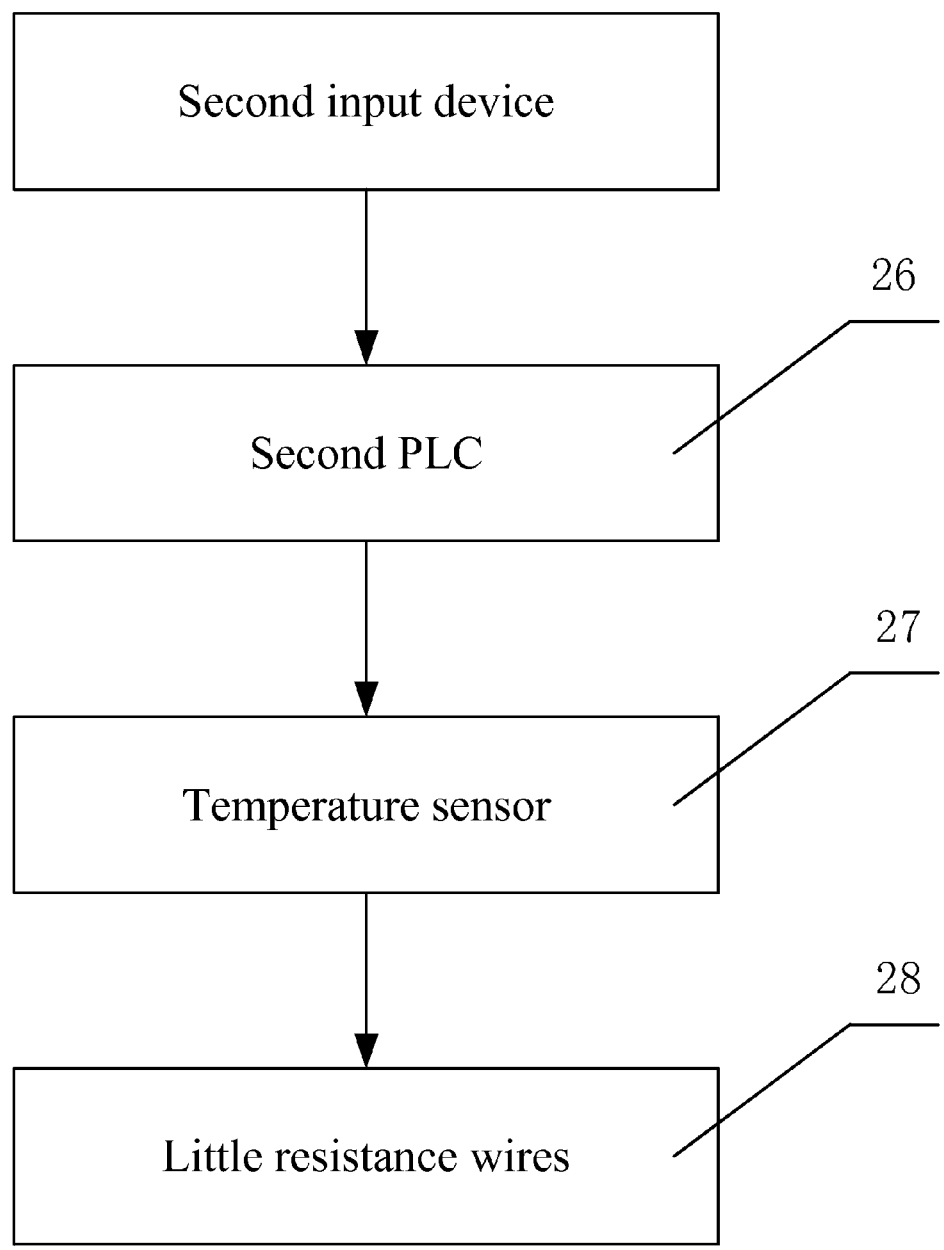
FIG. 4 is a block diagram showing a procedure control of heating PEEK material for preparing bones of cerebral cranium.

The heating device discriminatively heats different areas of the PEEK material to meet the requirements of temperature and strain force for material deformation according to the CT data of the patient, areas requiring a relatively large deformation are heated at a relatively high temperature, and areas requiring a relatively small deformation is heated at a relatively low temperature. The heating is controlled through a second PLC, a temperature sensor, and little resistance wires, as shown in FIG. 4.

Figure 1:
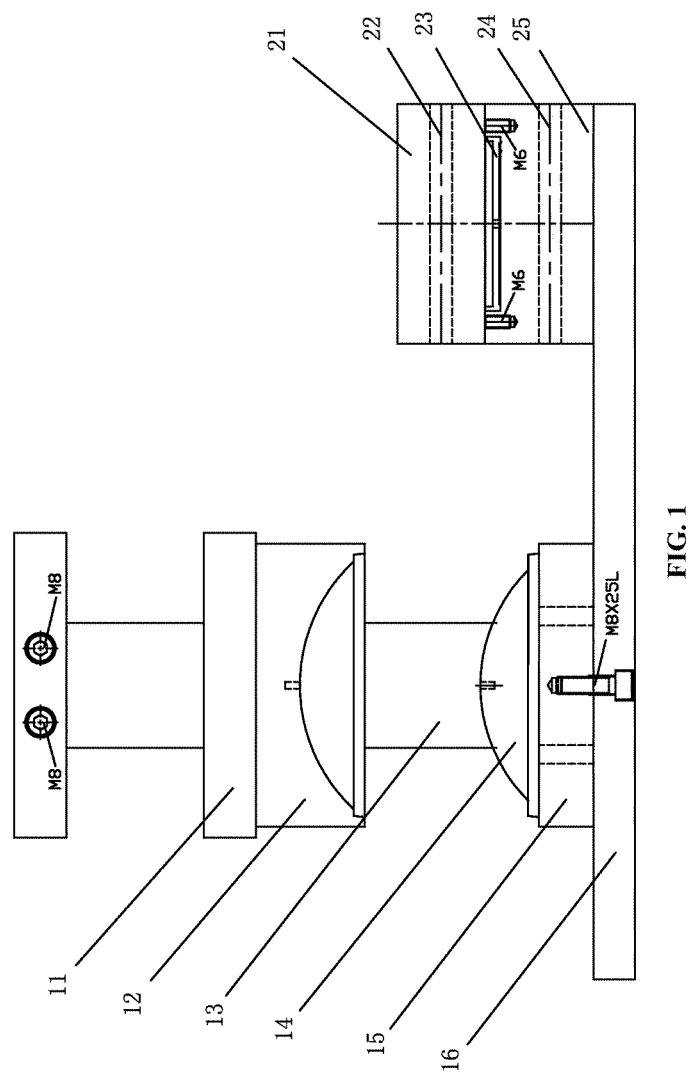
FIG. 1 is a schematic diagram of a device for preparing bones of cerebral cranium according to one embodiment of the invention.
Figure 2:
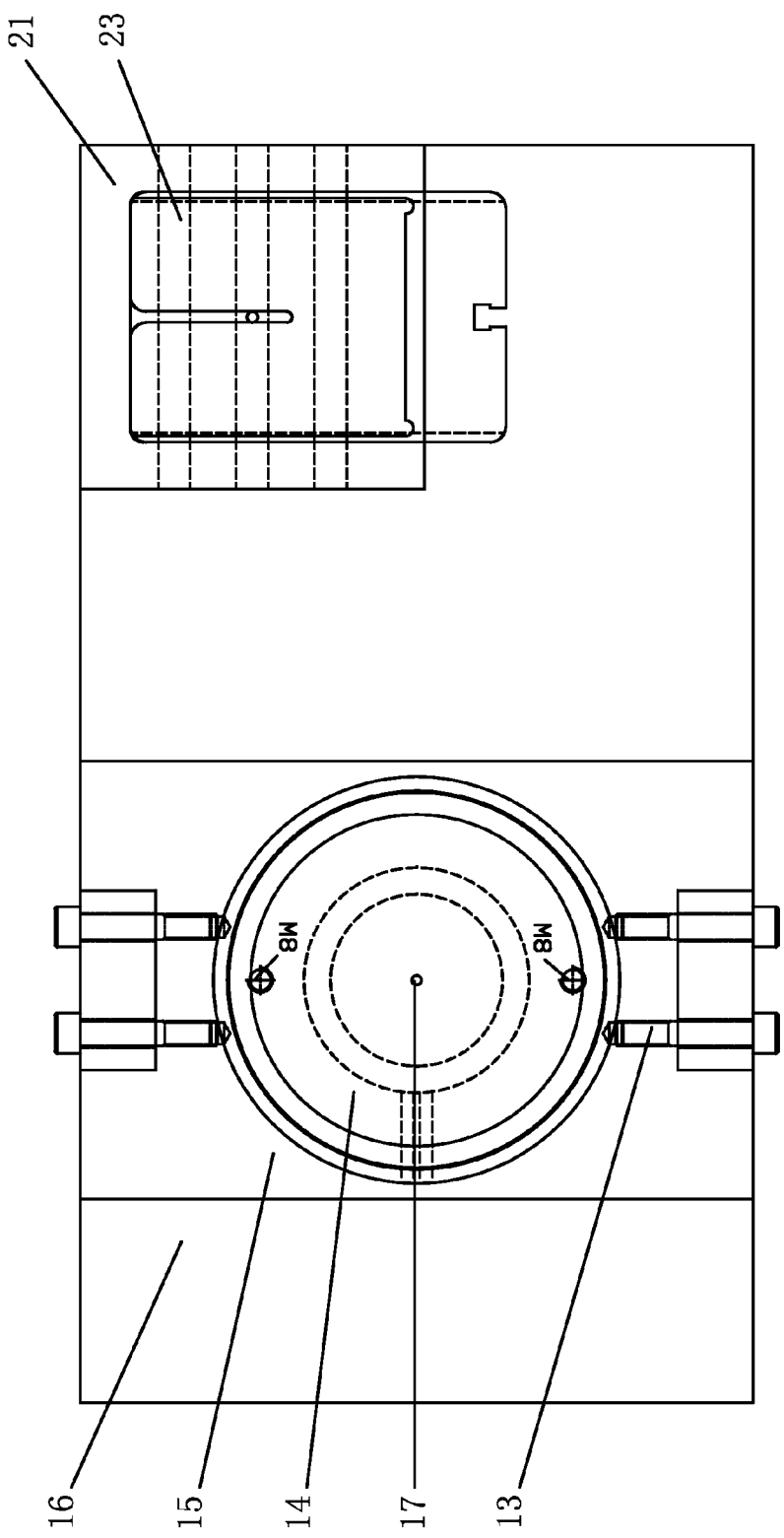
FIG. 2 is a top view of a device for preparing bones of cerebral cranium in the absence of an upper mold according to one embodiment of the invention.
Figure 3:
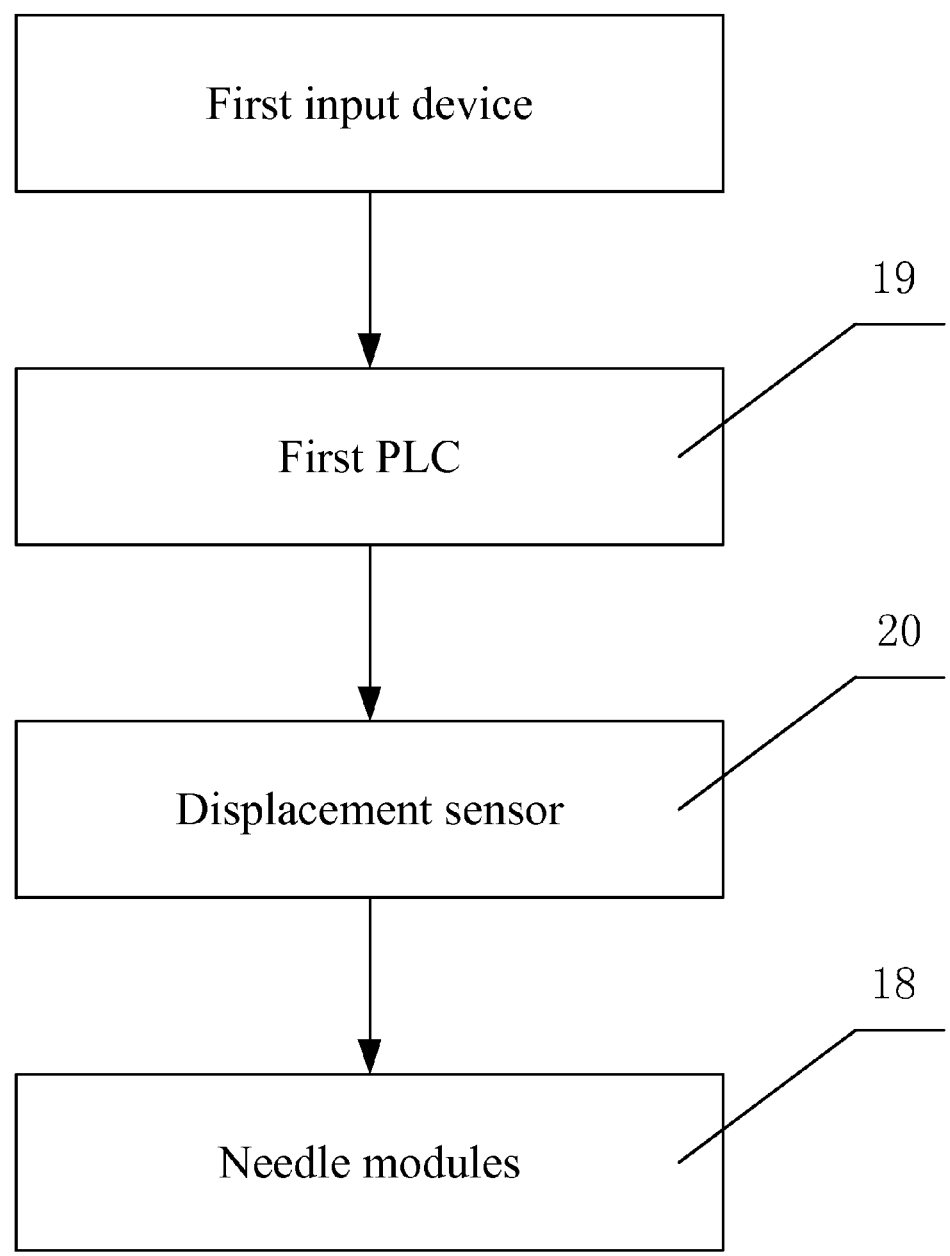
FIG. 3 is a block diagram showing a procedure control of shaping PEEK material for preparing bones of cerebral cranium.

The forming die comprises an upper mold comprising an upper needle module and a lower mold comprising a lower needle module. The lower needle module is controlled by a programmable logic controller (PLC) for space regulating and locating according to the CT data. The upper needle module is also regulated correspondingly, and thus the heated PEEK material is placed on the upper mold and processed by the upper and lower needle modules to yield the blank (as shown in FIG. 3).

A device for preparing bones of cerebral cranium comprises: a forming die and a heating device. The forming die comprises an upper mold base 11, an upper mold 12, a locating device 13, a lower mold 14, a lower mold base 15, and a base frame 16. The upper mold 12 is fixed on the upper mold base 11. The lower mold base 15 is fixed on the base frame 16 via a pin bolt 17. The upper mold 14 is fixed on the lower mold base 15, and a lower end of the locating device 13 is fixed on the base frame 16. The upper mold base 11 is fixed on the locating device 13, and a rear end of the upper mold base 11 is located in a sliding groove of the locating device 13. The upper mold 12 and the lower mold 14 each comprises a plurality of needle modules 18. The needle modules 18 are controlled by a first PLC 19 via a displacement sensor 20. The locating device 13 is perpendicular to the base frame 16.

The heating device comprises an upper cover plate 21, an upper heater 22, a support bracket 23, a lower heater 24, and a base 25. The support bracket 23 is disposed between the upper heater 22 and the lower heater 24. The upper heater 22 is disposed under a central area of the upper cover plate 21, and the lower heater 24 is disposed over a central area of the base 25. The upper heater 22 and the lower heater 24 each comprises a plurality of independent little resistance wires 28, and a second PLC 26 is connected to the little resistance wires 28 via a temperature sensor 27 (as shown in FIGS. 1-4).

EXAMPLE

Five healthy adult dogs without skull defects were sampled. Take CT photos from different sample points of the skulls of the five dogs, and collect the CT data. Thereafter, the following steps were carried out: a) selecting polyetheretherketone (PEEK) as a raw material according to computed tomography (CT) data of a patient; b) heating the PEEK material in a heating device to reach a softening point of 260°±10°; c) hot pressing the heated PEEK material obtained in step b) in a forming die, cooling and shaping the PEEK material to yield a blank; d) curing the blank, and placing the blank in a thermostat for removal of internal stress and resilience; e) removing surface crystals and impurities of the blank resulting from the hot pressing; f) mechanically processing the blank according to the CT data of the patient to yield a product having desired size and shape; and g) washing, disinfecting, and packaging the product.

The heating device discriminatively heats different areas of the PEEK material to meet the requirements of temperature and strain force for material deformation according to the CT data of the patient, areas requiring a relatively large deformation are heated at a relatively high temperature, and areas requiring a relatively small deformation is heated at a relatively low temperature. The heating is controlled through a second PLC, a temperature sensor, and little resistance wires, as shown in FIG. 4.

The forming die comprises an upper mold comprising an upper needle module and a lower mold comprising a lower needle module. The lower needle module is controlled by a programmable logic controller (PLC) for space regulating and locating according to the CT data. The upper needle module is also regulated correspondingly. The heated PEEK material is placed on the upper mold and processed by the upper and lower needle modules to yield the blank (as shown in FIG. 3).

The five dogs were performed with craniotomy, respectively, at the preset sample points of the skulls. The parts of the skulls were taken out and replaced by the PEEK bones of cerebral cranium. Thereafter, the soft tissue was refilled and epidermis sutured, both were confirmed by CT examination. Observe the recovery of the dogs in the first month, the third month, and the sixth month. The results showed that no heterotopia, deformation, and rejection reaction occurred. Six months later, the five dogs recovered as well as normal dogs.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing bones of cerebral cranium, the method comprising:
 a) selecting polyetheretherketone (PEEK) as a raw material according to computed tomography (CT) data of a patient;
 b) heating the PEEK material in a heating device to reach a temperature of 260°±10° C.;
 c) hot pressing the heated PEEK material obtained in step b) in a forming die, cooling and shaping the PEEK material to yield a blank;
 d) curing the blank, and placing the blank in a thermostat for removal of internal stress and resilience;
 e) removing surface crystals and impurities of the blank resulting from the hot pressing;
 f) mechanically processing the blank according to the CT data of the patient to yield a product having desired size and shape; and
 g) washing, disinfecting, and packaging the product.

* * * * *